(12) United States Patent
Haldar et al.

(10) Patent No.: US 12,561,870 B2
(45) Date of Patent: Feb. 24, 2026

(54) REGION-OPTIMZED VIRTUAL (ROVir) COILS

(71) Applicant: UNIVERSITY OF SOUTHERN CALIFORNIA, Los Angeles, CA (US)

(72) Inventors: Justin Haldar, Alhambra, CA (US); Daeun Kim, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 324 days.

(21) Appl. No.: 18/266,233

(22) PCT Filed: Dec. 13, 2021

(86) PCT No.: PCT/US2021/063138
§ 371 (c)(1),
(2) Date: Jun. 8, 2023

(87) PCT Pub. No.: WO2022/132659
PCT Pub. Date: Jun. 23, 2022

(65) Prior Publication Data
US 2024/0046533 A1 Feb. 8, 2024

Related U.S. Application Data

(60) Provisional application No. 63/127,046, filed on Dec. 17, 2020.

(51) Int. Cl.
*G06T 11/00* (2006.01)
*A61B 5/00* (2006.01)
(Continued)

(52) U.S. Cl.
CPC .......... *G06T 11/005* (2013.01); *A61B 5/0037* (2013.01); *G01R 33/5608* (2013.01);
(Continued)

(58) Field of Classification Search
CPC ............. G06T 2210/41; G06T 11/005; G01R 33/56572; G01R 33/5611; G01R 33/5608; A61B 5/0037
See application file for complete search history.

(56) References Cited

U.S. PATENT DOCUMENTS

2016/0025833 A1 1/2016 Polimeni et al.
2017/0199261 A1* 7/2017 Farr ................. G01R 33/56509
(Continued)

FOREIGN PATENT DOCUMENTS

CN 106597333 5/2016
EP 3751301 12/2020

OTHER PUBLICATIONS

International Search Report and Written Opinion for International PCT Patent Application No. PCT/US2021/063138, Apr. 12, 2022.
Zheng, et al. Coil combination using linear deconvolution in k-space for phase imaging. Quantitative imaging in medicine and surgery, 2019, vol. 9, No. 11, pp. 1792-1803.
(Continued)

*Primary Examiner* — John R Wallace
(74) *Attorney, Agent, or Firm* — Snell & Wilmer LLP

(57) ABSTRACT
Systems and methods of image reconstruction are provided. A system may have a memory and a processor to receive data corresponding to magnetic resonance imaging coils and data corresponding to a region of interest within a field of view of the magnetic resonance imaging machine. By determining different weights to associate with virtualized magnetic resonance imaging coils, images may be reconstructed to favor signals associated with a region of interest and to disfavor interference associated with areas outside the region of interest.

18 Claims, 10 Drawing Sheets

(51) Int. Cl.
    *G01R 33/56*     (2006.01)
    *G01R 33/561*    (2006.01)
    *G01R 33/565*    (2006.01)

(52) U.S. Cl.
    CPC .... *G01R 33/5611* (2013.01); *G01R 33/56572*
                (2013.01); *G06T 2210/41* (2013.01)

(56)              References Cited

U.S. PATENT DOCUMENTS

| | | | |
|---|---|---|---|
| 2019/0346518 A1 | 11/2019 | Lingala et al. | |
| 2021/0212567 A1* | 7/2021 | Sijbers | G06T 3/4053 |
| 2021/0295474 A1* | 9/2021 | Wang | G06N 3/084 |

OTHER PUBLICATIONS

The extended European search report and the European search opinion dated Sep. 17, 2024 in corresponding European Application No. EP21907575.1-1122; 8 pages.

Martin Buehrer et al; "Array Compression for MRI With Large Coil Arrays"; Magnetic Resonance in Medicine; Wiley-Liss, US; vol. 57, No. 6; Jun. 1, 2007; 9 pages; XP007908560.

Sagar Mandava et al; "Radial streak artifact reduction using phased array beamforming"; Magnetic Resonance in Medicine; vol. 81, No. 6; Feb. 12, 2019, 9 pages; XP093203176.

Yinqun Xue et al; "Automatic Coil Selection for Streak Artifact Reduction in Radial MRI"; Magnetic Resonance in Medicine: vol. 67, No. 2; Jun. 7, 2011; 7 pages; XP055027464.

Stephen Cauley et al; "Geometric Coil Mixing (GCM) to Dampen Confounding Signals in MRI Reconstruction"; International Society for Magnetic Resonance in Medicine, ISMRM, US; No. 449; Apr. 26, 2019; 6 pages; XP040707836.

* cited by examiner

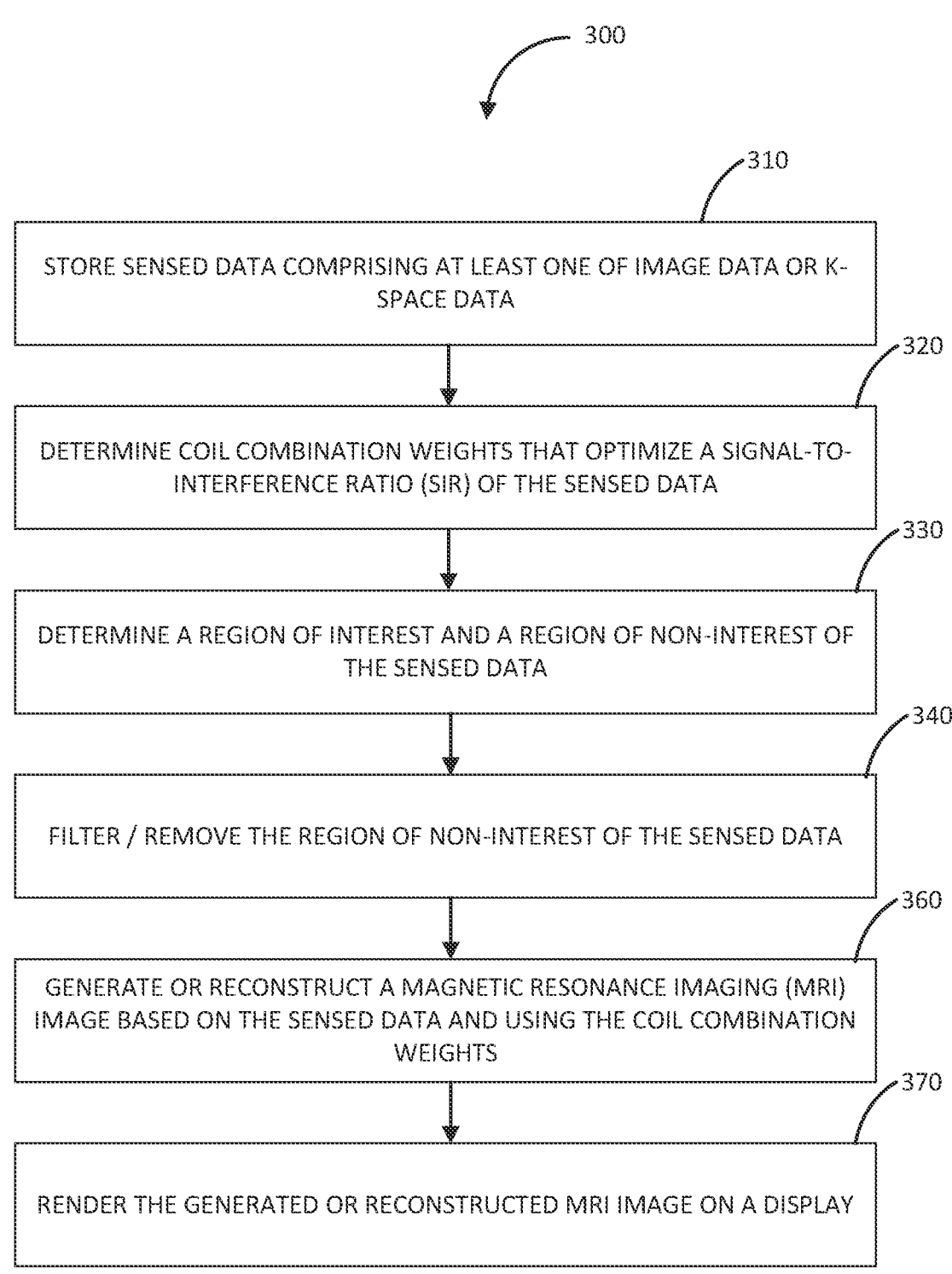

300

310

STORE SENSED DATA COMPRISING AT LEAST ONE OF IMAGE DATA OR K-SPACE DATA

320

DETERMINE COIL COMBINATION WEIGHTS THAT OPTIMIZE A SIGNAL-TO-INTERFERENCE RATIO (SIR) OF THE SENSED DATA

330

DETERMINE A REGION OF INTEREST AND A REGION OF NON-INTEREST OF THE SENSED DATA

340

FILTER / REMOVE THE REGION OF NON-INTEREST OF THE SENSED DATA

360

GENERATE OR RECONSTRUCT A MAGNETIC RESONANCE IMAGING (MRI) IMAGE BASED ON THE SENSED DATA AND USING THE COIL COMBINATION WEIGHTS

370

RENDER THE GENERATED OR RECONSTRUCTED MRI IMAGE ON A DISPLAY

FIGURE 3

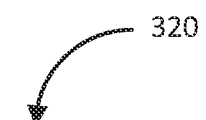
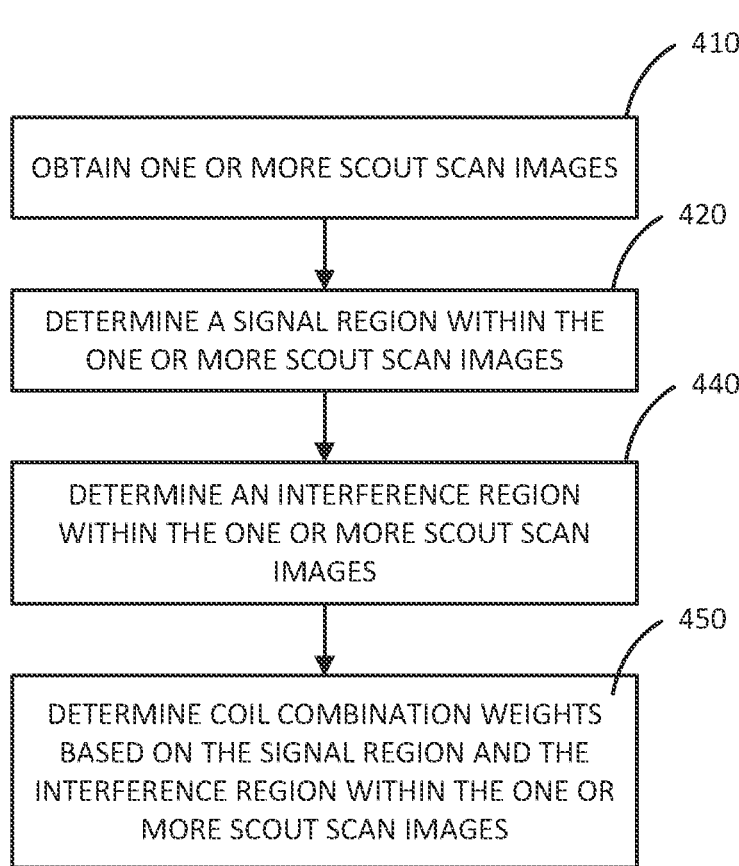
FIGURE 4

650
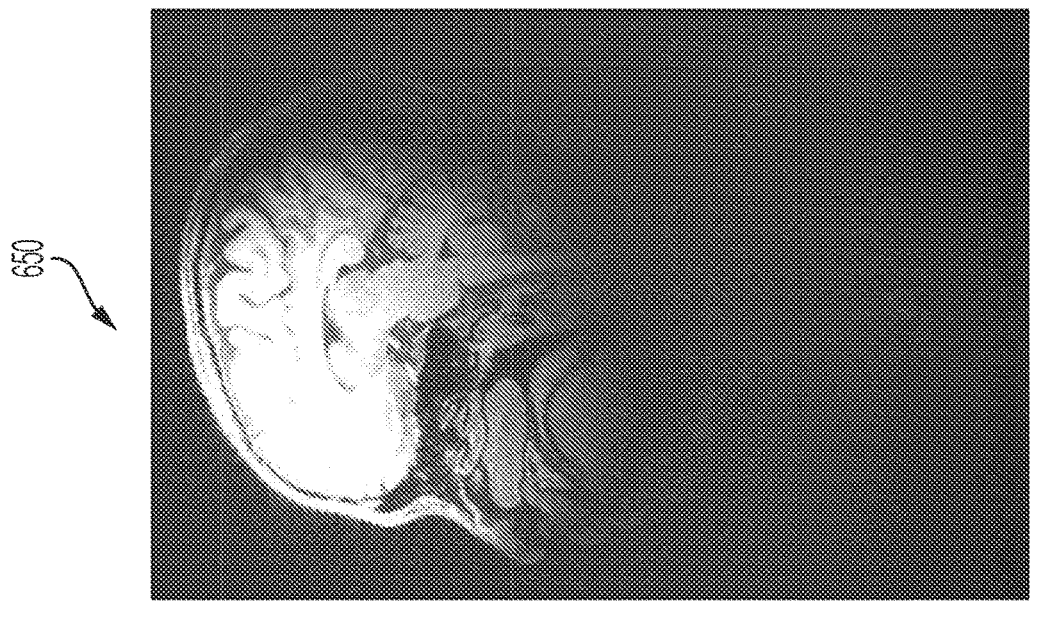
FIGURE 6B
600
610
620
630
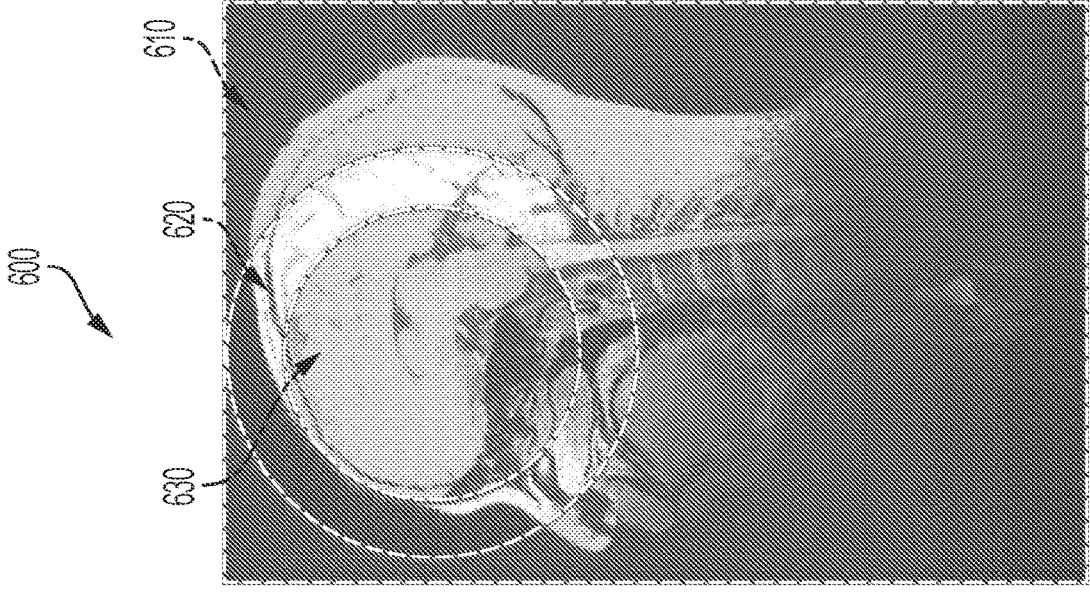
FIGURE 6A

REGION-OPTIMZED VIRTUAL (ROVir) COILS

CROSS-REFERENCE TO RELATED APPLICATIONS

This application is based upon and claims priority to U.S. provisional patent application 63/127,046 entitled "REGION-OPTIMIZED VIRTUAL (ROVir) COILS" and filed Dec. 17, 2020, the entire content of which is incorporated herein by reference.

GOVERNMENT LICENSE RIGHTS

This invention was made with government support under contract numbers R01-MH116173, R01-NS074980, R01-NS089212, and R33-CA225400 awarded by the National Institutes of Health (NIH). The government has certain rights in this invention.

FIELD

The present disclosure relates generally to magnetic resonance imaging, and more specifically, to region-optimized virtual coils for enhancing magnetic resonance imaging.

BACKGROUND

In many MRI scenarios, magnetization is often excited from spatial regions that are not of immediate interest. Excitation of uninteresting magnetization can complicate the design of efficient imaging methods, leading to either artifacts or acquisitions that are longer than necessary. Thus, there is a need for a system and method to suppress signals from unwanted regions without modifying the acquisition hardware or pulse sequence, improving accuracy, speed, and precision of MRI imaging.

SUMMARY

An image reconstruction system is provided. The image reconstruction system may include a memory and a processor. The memory may be configured to store image data or k-space data. The processor may be coupled to the memory. The processor may be configured to determine a region of interest of the image data or the k-space data. The processor may be configured to determine coil combination weights that optimize a signal-to-interference ratio of the image data or the k-space data based on the region of interest. Moreover, the processor may be configured to generate or reconstruct a magnetic resonance imaging (MRI) image or k-space data based on the image data or the k-space data and using the coil combination weights.

The image reconstruction system may have further aspects. For instance, the image reconstruction system may include a display. The display may be configured to render the generated or reconstructed MRI image. The processor is configured to output the generated or reconstructed MRI image on the display. In various instances, the generated or reconstructed MRI image is generated faster than a second generated or reconstructed MRI image generated from the entire k-space data and with the same resolution. In various instances, the generated or reconstructed MRI image is generated with greater resolution and during a same period of time than a second generated or reconstructed MRI image generated from the entire k-space data and with less resolution. Moreover, in certain scenarios, the generated or reconstructed MRI image is generated with fewer artifacts than a second generated or reconstructed MRI image generated from the entire k-space data.

The processor may be configured to determine a region of non-interest of the image data or the k-space data which is used to influence the determination of the coil combination weights. The processor may be configured to filter, remove, or attenuate the region of non-interest of the image data or the k-space data from the image data or the k-space data and exclude or suppress the region of non-interest of the image data or the k-space data when generating or reconstructing the MRI image. Moreover, the processor may be configured to obtain one or more scout scan images, determine a signal region within the one or more scout scan images, determine an interference region within the one or more scout scan images, and determine the coil combination weights based on the signal region and the interference region within the one or more scout scan images. In one or more embodiments, the processor is configured to obtain user input that indicates the signal region or the interference region within the one or more scout scan images or apply artificial intelligence to determine the signal region or the interference region within the one or more scout scan images, wherein the processor is configured determine the signal region within the one or more scout scan images based on the user input or using the applied artificial intelligence.

The coil combination weights may be configured to prioritize the signal region over the interference region. To determine the coil combination weights, the processor may form a signal matrix based on the signal region, form an interference matrix based on the interference region, and determine the coil combination weights based on the signal matrix and the interference matrix using a generalized eigen decomposition function.

The image reconstruction system may include other features. For instance, the image reconstruction system may include the memory and the processor. The memory may be configured to store image data or k-space data. The processor may be coupled to the memory. The processor may be configured to determine the region of interest of the image data or the k-space data. The processor may be configured to determine coil combination weights that optimize the signal-to-interference ratio of the image data or the k-space data based on the region of interest. The processor may also be configured to generate or reconstruct a magnetic resonance imaging (MRI) image based on the region of interest of the image data or the k-space data and transmit the generated or reconstructed MRI image for display. The image reconstruction system may include the display configured to render the generated or reconstructed MRI image. In various instances, the processor is configured to determine a region of non-interest of the image data or the k-space data which is used to influence the determination of the coil combination weights. Moreover, the processor may be configured to filter, remove, or attenuate the region of non-interest of the image data or the k-space data from the image data or the k-space data. The processor may further exclude or suppress the region of non-interest of the image data or the k-space data when generating or reconstructing the MRI image. In various instances, the processor is configured to obtain one or more scout scan images, determine a signal region within the one or more scout scan images, determine an interference region within the one or more scout scan images, and determine the coil combination weights based on the signal region and the interference region within the one or more scout scan images. The processor may be configured to obtain user input that indicates the signal region or the interference region within the one or more scout scan images, wherein the processor is configured determine the signal region within the one or more scout scan images based on the user input.

The image reconstruction system may have a magnetic resonance imaging (MRI) scanner configured to obtain the image data or the k-space data, wherein the image data or the k-space data is representative of data related to a human body. The data related to the human body may include biological, anatomical, neurological functional, microstructural, or physiological data of the human body.

A method of generating a magnetic resonance imaging (MRI) image is provided. The method may include obtaining, by a processor, image data or k-space data. The method may include determining, by the processor, a region of interest of the image data or the k-space data. The method may include determining, by the processor, coil combination weights that optimize a signal-to-interference ratio of the image data or the k-space data based on the region of interest. Finally, the method may include generating or reconstructing, by the processor, the MRI image based on the image data or the k-space data using coil combination weights.

BRIEF DESCRIPTION OF THE DRAWINGS

The subject matter of the present disclosure is particularly pointed out and distinctly claimed in the concluding portion of the specification. A more complete understanding of the present disclosure, however, is best be obtained by referring to the detailed description and claims when considered in connection with the drawing figures, wherein like numerals denote like elements.

FIGS. 2 and 3 depict aspects of example methods of image reconstruction via region-optimized virtual coil (ROVir) analysis, in accordance with various embodiments;

FIG. 4 depicts aspects of a method for determining coil combination weights that optimize a signal-to-interference ratio of sensed data, in accordance with various embodiments;

FIGS. 6A-B depict illustrations of steering a virtual array toward spatial locations with a region of interest, in accordance with various embodiments;

DETAILED DESCRIPTION

Figure 1:
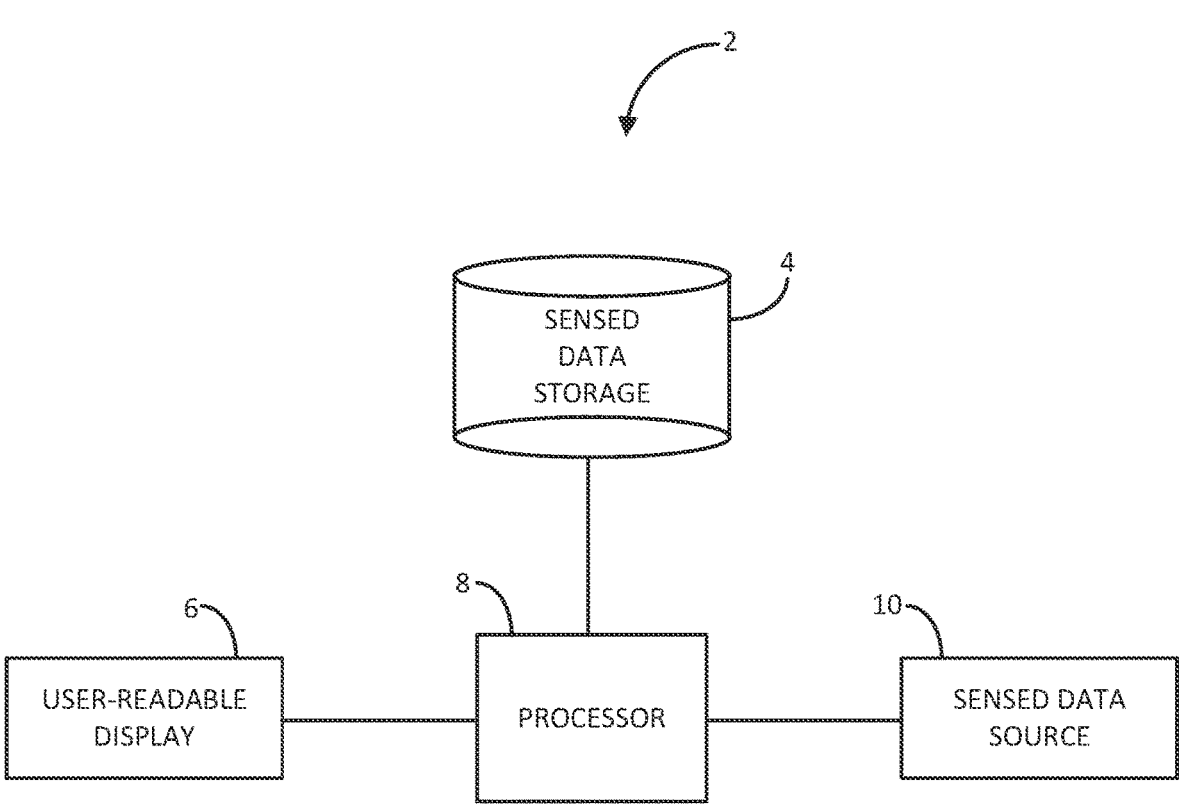
FIG. 1 depicts an example embodiment of an image reconstruction system for performing region-optimized virtual coil (ROVir) analysis, in accordance with various embodiments.

A system, apparatus and/or method for optimizing magnetic resonance imaging (MRI) images of a region of interest (ROI) of a specimen by improving data acquisition of the signals corresponding to the region of the interest using region-optimized virtual coils (ROVir coils) is described as set forth in herein. In various instances, beamforming is implemented to suppress signals from unwanted regions without modifying the acquisition hardware or pulse sequence. Thus, a spatially-invariant sensor-domain approach is provided that can be applied directly to raw data to facilitate image reconstruction. The disclosure herein will implement beamforming to linearly mix a set of original coils into a set of region-optimized virtual (ROVir) coils. ROVir coils optimize a signal-to-interference ratio metric, are easily calculated using simple generalized eigenvalue decomposition methods, and provide coil compression. In addition, ROVir coils will be discussed herein in comparison against existing coil-compression methods and are demonstrated to have substantially better signal suppression capabilities. ROVir coils may be implemented in a variety of different application contexts. For instance, ROVir coil technology may be implemented in the context of brain MRI, vocal tract MRI, and cardiac MRI, accelerated cartesian and non-cartesian imaging, and outer volume suppression, among other contexts.

MRI experiments are often designed to provide information about a specific spatial region of interest (ROI) inside the body. However, instead of only acquiring data and reconstructing images corresponding to the ROI, typical MRI acquisitions often reconstruct much larger spatial regions, including regions that can be uninteresting for the target application.

These uninteresting spatial regions are often encoded and reconstructed in an effort to avoid artifacts. A conventional magnetic resonance receiver coil does not discriminate between interesting and uninteresting spatial regions and will detect signal from all of the excited magnetization within the sensitive region of the coil. Uninteresting magnetization that has been excited cannot be ignored. If it is not adequately spatially-encoded and reconstructed, signal from uninteresting regions can leak or alias into other spatial regions, potentially contaminating the reconstruction of the desired ROI.

Encoding and reconstructing uninteresting image regions can be inefficient and burdensome for data acquisition. For example, standard MRI sampling theory dictates that reconstructing a larger field-of-view (FOV) necessitates increased k-space sampling density requirements. Conversely, it is also understood that spatial encoding requirements and image reconstruction complexity can be substantially reduced if the received signal only originates from a small spatially-localized ROI.

Because of these issues, substantial effort has been spent within the magnetic resonance community to avoid signal from uninteresting spatial regions in order to simplify other aspects of experiments. Examples include the development of methods that only produce a consistent homogeneous $B_0$ main magnetic field at a single spatial point within the object, the use of localized surface coils that are designed to focus on a specific spatial ROI, the development of spatially-selective radiofrequency excitation methods that only excite magnetization from a specific ROI, allowing for "zoomed," "inner volume," "single voxel," "line scan," "slice selective," or "reduced field-of-view" imaging, and outer volume suppression methods designed to saturate the signal from uninteresting spatial regions.

Advantageously, systems and methods disclosed herein are operable to suppress a signal from uninteresting spatial regions without requiring modification of MRI receiver hardware or acquisition pulse sequencing, in contrast to prior efforts. Systems and methods herein generally identify simple linear combinations of the sensor-domain data obtained from an array of receiver coils that optimally suppress the unwanted signal. These linear combinations are designed to produce region-optimized virtual (ROVir) coils that simultaneously maximize the signal energy observed from interesting spatial regions and minimize the signal energy observed from undesired spatial regions.

Importantly, these operations can be applied in the sensor domain (e.g., to the raw multi-channel k-space data prior to image reconstruction), which enables reduced k-space data sampling requirements and simplified image reconstruction. Moreover, this approach for generating ROVir coils is computationally efficient as it includes the specification of interesting and uninteresting spatial regions and the computation of a small generalized eigenvalue decomposition.

Moreover, the ROVir approach is also optimal with respect to an intuitive signal-to-interference ratio (SIR) metric that represents the ratio between signal energy from the spatial region of interest (ROI) and the interference energy from unwanted signal regions (region of non-interest).

The system and method disclosed herein includes synthesizing virtual coils as linear combinations of data from original coils, rather than working directly with the data from the original coils. Benefits include eliminating inter-channel noise correlation, compressing a large number of original real coils into a smaller number of virtual coils without loss of substantial information content, simplifying the use of k-space conjugate symmetry relationships in image reconstruction, and importantly, suppressing a signal from spatial regions of non-interest of the MRI scan.

Advantageously, the spatially-invariant sensor-domain beamforming mechanisms disclosed herein can be applied directly to raw multi-channel k-space data to facilitate image reconstruction, whereas prior spatially-varying image-domain beamforming efforts merely provide an image post-processing technique that cannot be applied directly to raw multi-channel k-space data to facilitate the image reconstruction process.

Further advantageously, unlike prior coil selection methods, the novel implementation of virtual coils refrains from discarding channels from the original array. By refraining from discarding channels from the original array, virtual coil technology permits greater flexibility and better SIR than could generally be achieved by coil selection.

Turning attention to FIG. 1, one example embodiment of an image reconstruction system for performing region-optimized virtual coil (ROVir) analysis may comprise a collection of memory, processing, display and other components to ingest data, store data, process data, and generate a user readable display output.

For instance, a processor 8 may be provided. The processor 8 may comprise a computer processor capable of performing computations. The processor 8 may be connected to a sensed data source 10. In various embodiments, the sensed data source 10 is an MRI scanner. In further instances, the sensed data source 10 is a repository of data corresponding to MRI scanner outputs. The sensed data source 10 may provide data corresponding to MRI imagery to the processor 8.

The processor 8 may be connected to a sensed data storage memory 4. In various instances, processing by the processor 8 of data may happen asynchronously with data collection. In further instances, processing by the processor 8 of data may happen synchronously with data collection. In either instance, sensed data storage memory 4 may comprise an electronic memory for the storage of sensed data from the sensed data source 10 and/or may comprise a working memory for storage of variables and the results of computations during data processing by the processor 8.

Finally, the processor 8 may be connected to a user-readable display 6. The user-readable display 6 may comprise any human-machine interface configured to represent processed data processed by the processor 8 in a human-interpretable form. In various instances, user-readable display 6 comprises a computer display terminal depicting images.

The processor 8 may perform computations to prepare data from the sensed data source 10 for display and interpretation on the user-readable display 6. While the following discussion will elaborate in detail on these techniques, brief reference to FIGS. 1 and 2 introduces the system and a method for image reconstruction 20 prior to the more specific discussion of example embodiments.

Original coils data 22 corresponding to data from actual coils of an MRI scanner may be ingested by a processor 8. In addition, data identifying signal and interference regions 34 (regions of interest and regions of non-interest, respectively) may be ingested by the processor 8.

A matrix may be formed from both sets of data. An A-matrix 24 may be generated corresponding to the original coils data 22 and a B-matrix 36 may be generated corresponding to the data identifying signal and interference regions 34. The data identifying signal and interference regions (ROI and region of non-interest, respectively) may be user-provided or may be determined by an implementation of artificial intelligence technology in the processor 8.

A generalized eigen decomposition 26 may be performed on the A-matrix and B-matrix. Combination weights 28 may be calculated and applied to the output of the generalized eigen decomposition 26, to weight the data in favor of the ROI, providing an enhanced signal-to-interference ratio (SIR). This weighted data forms virtual coils data 30 corresponding to a virtualized set of coils of an MRI scanner advantageously favoring signal from the ROI. More specifically, this virtual coils data 30 can be manipulated to provide imagery for a first subset of the virtual coils 32 and imagery for a second subset of the virtual coils 40. The first subset imagery may correspond to the region of interest (ROI) while the second subset imagery may correspond to the region of non-interest.

Having briefly introduced the operations of a system and method for image reconstruction by performing ROVir coil analysis, the discussion will now elaborate in detail on these techniques. For simplicity and without loss of generality, the following detailed discussion will describe ROVir coil analysis in the context of a standard sensitivity-encoded (SENSE) Fourier imaging model, although the same principles also generalize naturally to non-Fourier models (including field inhomogeneity, relaxation, nonlinear gradient fields, etc.) of multichannel data acquisition. Under this model, the k-space data measured from the $\ell$th coil at k-space location k is given by $d_\ell(k)=\int s_\ell(x)f(x)e^{-i2\pi k \cdot x}dx + n_\ell(k)$ (1) for $\ell=1, \ldots, N_c$, where $f(x)$ represents the complex-valued magnetic resonance image as a function of the spatial position x, $s_\ell(x)$ is the complex-valued spatial sensitivity profile of the $\ell$th receiver coil, $N_c$ is the total number of coils in the receiver array, and $n_\ell(k)$ represents the thermal measurement noise associated with the $\ell$th receiver coil. In various instances, the data may have been precedingly whitened, such that the inter-coil noise covariance matrix $\Psi$ is simply the $N_c \times N_c$ identity matrix and all noise samples can be modeled as independent and identically distributed zero-mean complex Gaussian random variables.

In various instances, the measured data (original coils data 22) may contain information from the sensitivity weighted image arising from spatial locations x that are outside the ROI. This may be problematic because the signal from these spatial locations may interfere with data acquisition and image reconstruction from the spatial regions of interest. As a result, the measured data samples $d_\ell$ (k) from each coil can be represented as a mixture of useful signal from the ROI together with unwanted signal from other spatial locations ("interference").

By implementing beamforming as disclosed herein, instead of working directly with the data from the original coils 22, systems and methods work with data from virtual coils 30. This virtual coil data 30 is obtained from linear combinations of the original coils, where the linear combination weights are designed in an optimal way to maximize signal and minimize interference.

Consider the scenario in which the k-space data $d_\ell$ (k) from a set of $N_c$ original coils are linearly transformed into data from a set of $N_v$ virtual coils according to $V_j(k) = \sum_{\ell=1}^{N_c} w_{\ell j} d_\ell$ (k)(2) for j=1, ..., $N_v$, where $v_j(k)$ is the k-space data for the jth virtual coil and the complex-valued scalars $\{w_{\ell j}\}$ are the linear combination weights. By inserting Eq. (2) into Eq. (1) and rearranging terms, one may appreciate that these new virtual coils obey a sensitivity-weighted Fourier encoding model that is similar to Eq. (1), except with different sensitivity profiles and noise values. In particular, $v_j(k) = \int \tilde{s}_j$ (x)$f$(x)$e^{-i2\pi k \cdot x}$dx+$\tilde{n}_j$(k) (3), with $\tilde{s}_j(x) = \sum_{\ell=1}^{N_c} w_{\ell j} s_\ell$ (x) (4), and $\tilde{n}_j(k) = \sum_{\ell=1}^{N_c} w_{\ell j} n_\ell$ (k) (5) for each virtual coil j.

Importantly, an appropriate choice of the weighting coefficients $\{w_{\ell j}\}$ allows the sensitivity profiles $\tilde{s}_j(x)$ of the virtual array to be steered towards spatial locations within the ROI and away from unwanted spatial locations. An illustration of what can be achieved with this kind of steering is presented in FIGS. 6A, 6B. As can be seen, the ROI 630 of FIG. 6A is reproduced with precision and accuracy in FIG. 6B which represents data processed according to the system and method herein. At the same time, unwanted signal 610 from outside the ROI is suppressed in FIG. 6B. A transition area 620 is depicted interstitially between the ROI 630 and the unwanted signal 610.

It should be noted that while the sensitivity-based analysis above provides insight, in a practical implementation, it is not required that the system have knowledge of the sensitivity profiles $s_\ell$ (x) or $\tilde{s}_j(x)$.

Figure 2:
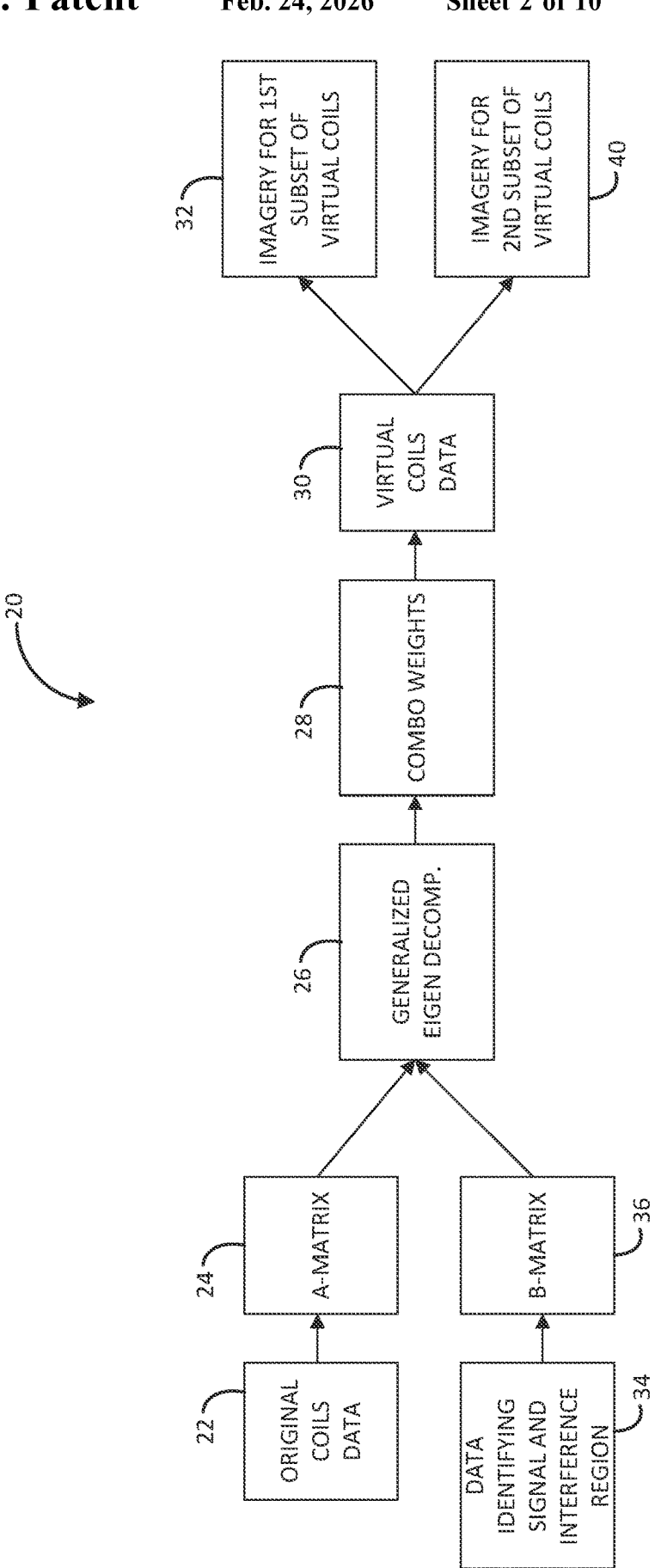

For instance, with renewed reference to FIGS. 1, and 2, a method of image reconstruction via region-optimized virtual coil (ROVir) analysis executed by the processor 8 on original coils data 22 from a sensed data source 10 proceeds illustratively from left to right in FIG. 2. In various embodiments, the weighting coefficients $\{w_{\ell j}\}$ are chosen to maximize an SIR metric, which is defined as the ratio between the signal energy from the spatial region of interest and the interference energy from unwanted spatial regions. In particular, $\Omega$ denotes the spatial ROI. The total k-space signal energy in the jth virtual coil arising from the ROI is defined using Parseval's theorem as:

$$S(w_j) \triangleq \int_{x \in \Omega} |\tilde{s}_j(x) f(x)|^2 \, dx \qquad (6)$$

-continued
$$= \int_{x \in \Omega} \left| \sum_{\ell=1}^{N_c} w_{\ell j} g_\ell(x) \right|^2 dx$$
$$= w_j^H A w_j,$$

where $w_j \in \mathbb{C}^{N_c}$ is the vector of weighting coefficients $\{w_{\ell j}\}$ for $\ell = 1, ..., N_c$, $g_\ell$ (x)$\triangleq s_\ell$ (x)$f$(x) is the sensitivity weighted image for the $\ell$ th coil, and the matrix $A \in \mathbb{C}^{N_c \times N_c}$ is defined as A=$\int_\Omega$g(x)$^H$g(x)dx (7) with g(x)$\in \mathbb{C}^{1 \times N_c} \triangleq$ [g₁(x) $g_{N_c}$(x)] (8).

D interpreted as the inter-coil signal correlation matrix corresponding to the spatial region $\Omega$. Similarly, using $\Gamma$ to denote the spatial region containing unwanted information, the interference energy in the jth virtual coil arising from these unwanted spatial regions may be defined as:

$$I(w_j) \triangleq \int_{X \in \Gamma} |\tilde{s}_j(x) f(x)|^2 dx \qquad (9)$$
$$= w_j^H B w_j,$$

where the matrix $B \in \mathbb{C}^{N_c \times N_c}$ is defined as B=$\int_\Gamma$g(x)$^H$g(x)dx (10). As above, the B matrix 36 can be interpreted as the inter-coil signal correlation matrix corresponding to the spatial region $\Gamma$. Thus, data identifying signal and interference regions 34 may be processed by processor 8 to generate the B-matrix 36, while original coils data 22 may be processed by a processor 8 to generate the A-matrix 24.

Having defined both signal and interference, one may then define the signal-to-interference ratio (SIR) for the jth virtual coil as the ratio between the two:

$$SIR(w_j) \triangleq \frac{w_j^H A w_j}{w_j^H B w_j} \qquad (11)$$

Virtual coils are obtained by finding weight vectors $w_j$ that maximize this SIR criterion, thereby ensuring that the signal from the ROI is maximized while the interference is minimized.

Before describing the optimization of Eq. (11), it is worth noting that an interesting relationship between this SIR criterion and optimality criteria may also be used to construct virtual coils for the purpose of coil-compression. In particular, coil-compression methods may use singular value decomposition (SVD)/principal component analysis (PCA) to choose weight vectors that maximize the total amount of observed signal energy from the receiver array, without worrying about minimizing interference energy. In particular, it can be shown that the ROI-based version of optimal SVD/PCA coil-compression technique is equivalent to finding weight vectors that maximize:

$$SNR(w_j) \triangleq \frac{w_j^H A w_j}{w_j^H w_j}. \qquad (12)$$

As can be seen, the approach provided herein may include an SVD/PCA coil-compression approach when the B matrix is chosen as the identity matrix. Note also that if the interference region $\Gamma$ contains only whitened Gaussian noise, then the B matrix will be an empirical coil covariance matrix that is well-approximated by the identity matrix, and the approach will behave similarly to the SVD/PCA approach.

Techniques for choosing coil-combination weights that maximize the SIR from Eq. (11) may be provided. For instance, Eq. (11) has the form of a generalized Rayleigh quotient, and optimal weight vectors for this kind of optimization problem can be obtained using a generalized eigen decomposition.

Assume that A and B are both positive-semidefinite Hermitian-symmetric matrices, and that B has full rank. Then it can be shown that there exists a set of $N_c$ real-valued positive generalized eigenvalues $\lambda_i$ and a corresponding linearly-independent set of generalized eigenvectors $w_i$, i=1, . . . , $N_c$ that satisfy $Aw_i = \lambda_i Bw_i$ (13). Thus, the A-matrix 24 and the B-matrix 36 may be ingested by the processor 8 which performs a generalized eigen decomposition 26 and chooses optimal weight vectors (coil-combination weights 28).

These generalized eigenvalues and eigenvectors are computed using eigenvalue solvers, and a generalized eigenvector for the pair of matrices A and B must also be a standard eigenvector for the single matrix $B^{-1}A$. Notably, these generalized eigenvectors may be non-orthogonal (as was the case when applying SVD/PCA), which can have the consequence of introducing noise correlation between the resulting virtual channels as described below. Instead, the generalized eigenvectors are "B-orthogonal" in the sense that $w_j^H Bw_i = 0$ whenever i≠j.

Further, if the eigenvalues are ordered such that $\lambda_1 \geq \lambda_2 \geq \ldots \geq \lambda_{N_c} > 0$, then the first eigenvector $w_1$ maximizes the SIR criterion from Eq. (11) while the bottom eigenvector $w_{N_c}$ minimizes the SIR. Further, it can be shown that projecting the data onto the $N_v$-dimensional subspace spanned by the top-$N_v$ generalized eigenvectors $W_1$, . . . , $w_{N_v}$ is optimal in the sense that it maximizes the ratio between the retained signal energy and the retained interference energy among all possible $N_v$-dimensional subspace projections.

This leads to a methodology for choosing the $\{w_{\ell j}\}$ coefficients (needed to form optimal virtual coils). Such a methodology may include a process as follows. First, the method may include forming matrices A 24 and B 36 corresponding to Eqs. (7) and (10).

The method may include computing the generalized eigenvalue decomposition 26 for matrices A and B, and order the generalized eigenvalues and eigenvectors such that $\lambda_1 \geq \lambda_2 \geq \ldots \geq \lambda_{N_c} > 0$. The eigenvectors associated with distinct eigenvalues are unique up to scaling ambiguities, and it is convenient to work with unit-normalized versions of the eigenvectors such that $\|w_j\|_2 = 1$ for each j=1, . . . , $N_c$.

If noise-whitened virtual channels are desired, such whitening can be achieved by applying a simple Gram-Schmidt orthonormalization procedure to the top-$N_v$ generalized eigenvectors. Notably, the weight vectors $w_i$ and $w_j$ obtained from the generalized eigenvalue decomposition are unlikely to be orthogonal unless B happens to be a diagonal matrix. This means that there may be nonzero noise correlation between the different virtual coils, since the noise correlation between virtual channel i and virtual channel j will be equal to $w_j^H \Psi w_i = w_j^H w_i$. Note that this orthonormalization procedure does not change the subspace spanned by the top-$N_v$ generalized eigenvectors, and therefore does not change the optimality characteristics of the remaining steps. If this orthogonalization step is not utilized, then achieving optimal image SNR will generally require this new source of noise correlation to be properly accounted for if coil combination and/or multi-channel image reconstruction steps are subsequently applied to data.

The method may continue with using the top-$N_v$ generalized eigenvectors $w_j$ for j=1, . . . , $N_v$ (or their orthonormalized versions), to define the linear combination weights 28 according to $w_{\ell j} = [w_j]_\ell$.

The method contemplates forming virtual coil data 30 following Eq. (2).

One challenge associated with this method is that of forming the A and B matrices in the first step. The potential challenge in forming these matrices is that (1) it appears that prior knowledge of each of the individual sensitivity-weighted coil images $g_\ell(x)$ must be available and (2) it is necessary to integrate continuous-valued images.

However, both of these potential challenges are overcome by the system and methods herein. The first issue can be solved by forming images from prescan/calibration data and computing the optimal coil combination weights with respect to those images. The acquisition of prescan/calibration data is a part of some MRI protocols and the virtual coils obtained from such data has excellent SIR characteristics for any subsequent datasets as long as the relative spatial distribution of image energy is not substantially changed. The second potential challenge is also easily solved, noting that the integrals in Eqs. (7) and (10) are easily approximated with discrete sums over reconstructed voxels that fall within Ω (for Eq. [7]) or Γ (for Eq. [10]).

While the method herein is robust in practical implementations, one may appreciate that the generalized eigen decomposition procedure can be unstable if the matrix B is either rank-deficient or approximately rank deficient. In principle, this kind of problem could happen if the spatial region Γ is too small (e.g., fewer than $N_c$ voxels were used in the construction of the matrix B) or if the sensitivity maps do not have significant spatial variations within the region Γ. Thus, in various embodiments, mitigation approach is implemented to use simple regularization of B to ensure it has full numerical rank, e.g., replacing B with B+ξI, where I is the $N_c \times N_c$ identity matrix and ξ is a small positive constant.

In order to suppress the unwanted signal from the spatial region Γ, it is necessary to choose $N_v < N_c$, which has the practical effect of discarding those virtual coils with the lowest SIR (imagery for second subset of virtual coils 40) while retaining the virtual coils with the highest SIR (imagery for first subset of virtual coils 32). The mechanisms provided herein should not only be viewed as a signal-suppression method but can also be viewed as a coil compression method. Coil compression methods map a high-dimensional coil array into a much lower-dimensional coil array (e.g., imagery for a first and second subset of virtual coils 32, 40), resulting in substantial reductions in memory requirements and computational complexity for downstream image reconstruction.

Prior coil-compression approaches attempt to maximize the signal energy that is present in the top-$N_v$ virtual coils without considering interference. In contrast, the approach herein maximizes the SIR of the top-$N_v$ virtual coils. As a result, the approach herein exhibits tradeoffs wherein the approach theoretically guaranteed to be no better (and likely slightly worse) at preserving signal energy than traditional coil-compression methods, though is also theoretically guaranteed to have no worse (and likely much better) interference suppression characteristics.

Advantageously, the number of virtual channels $N_v$ does not need to be a user-selected parameter, and instead can be chosen automatically based on the quantitative signal and interference characteristics of each channel. In particular, given a weight vector $w_j$, it is straightforward to evaluate the signal and interference components for the corresponding virtual coil using Eqs. (7) and (10). Consequently, one may choose $N_v$ by only retaining the virtual coils that have sufficiently-high signal and sufficiently-low interference components. Examples shown later herein use different methods for automatically selecting $N_v$ based on several different application-dependent considerations (e.g., depending on whether it is more important to maximize signal or to minimize interference in the given application).

To evaluate the characteristics of systems and methods herein, the disclosed approach has been applied to different datasets representing several different imaging applications, including reduced-FOV brain imaging, reduced-FOV speech imaging, reduced-FOV cardiac imaging, and outer-volume suppression in the brain.

Figures 8A, 8B:
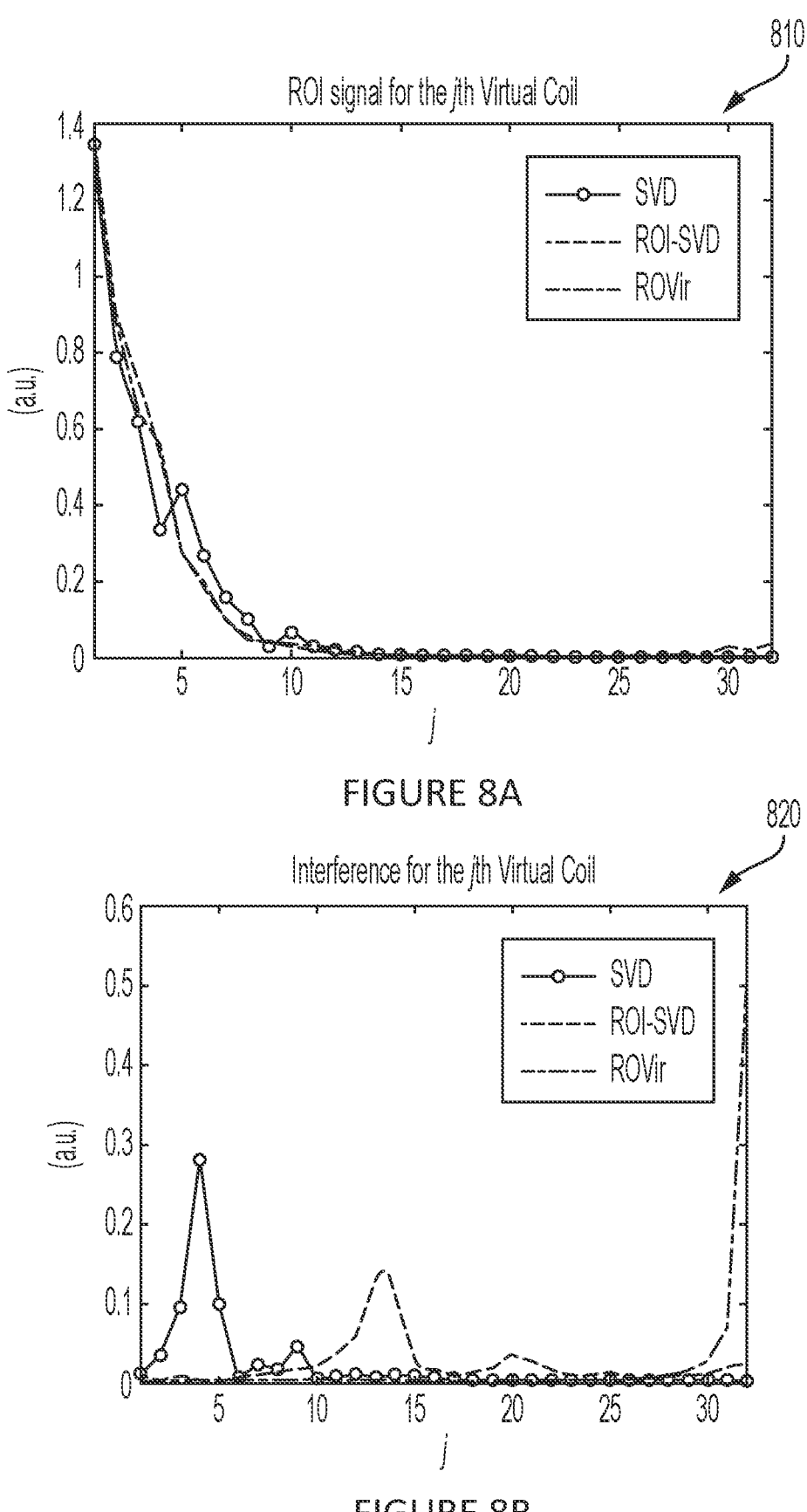
FIGS. 8A-C depict graphic representations of signal energy and interference energy of virtual coils, in accordance with various embodiments.
Figure 8C:
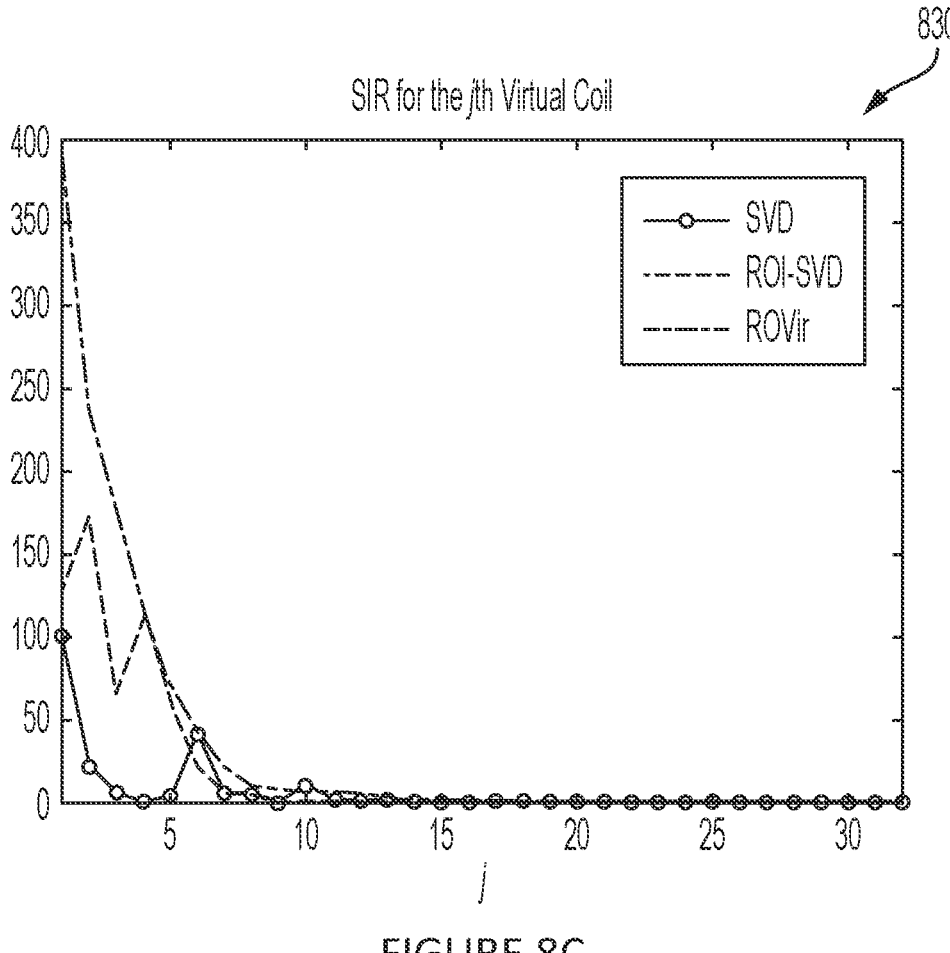
Figures 9A, 9B:
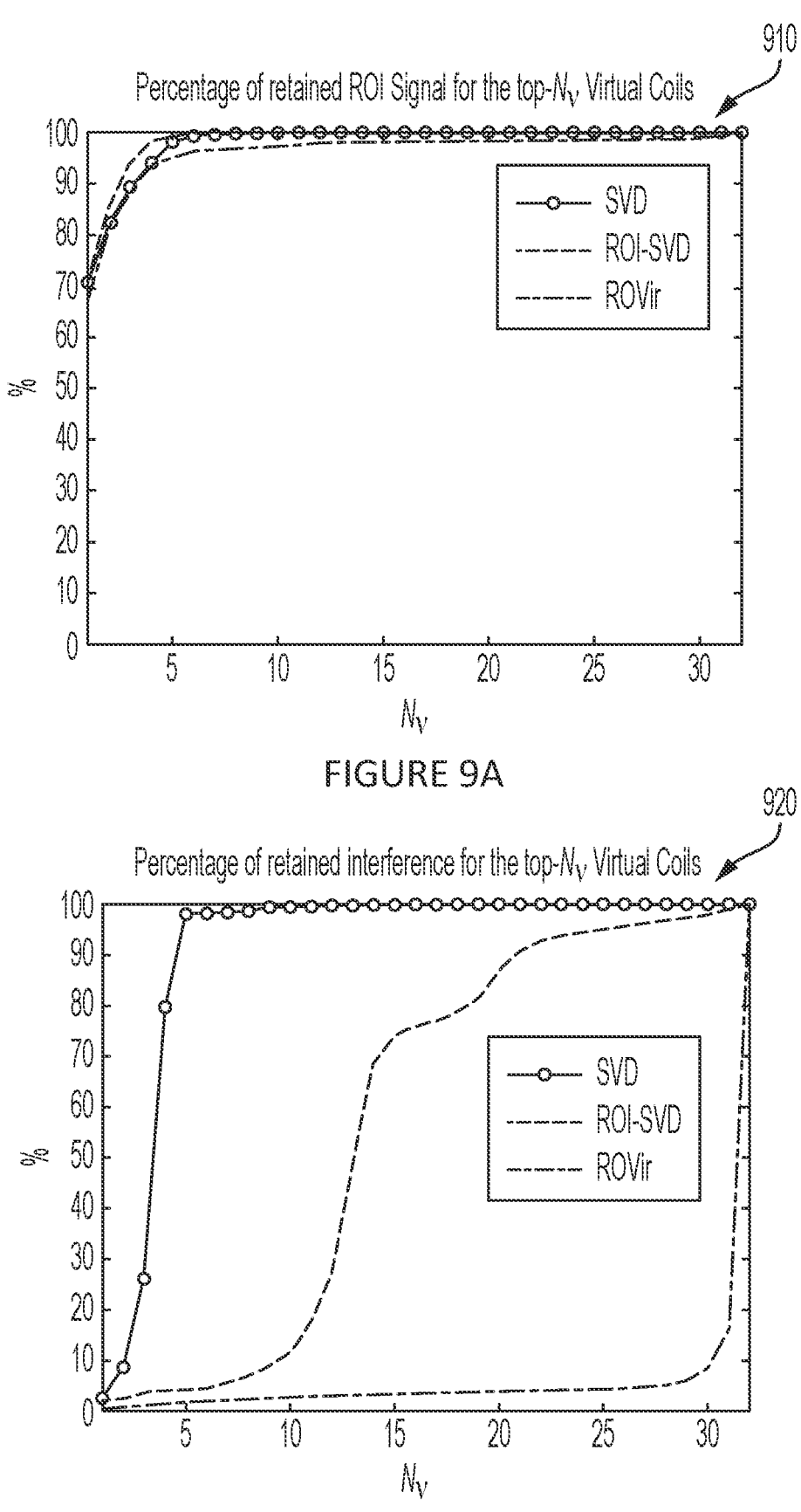
FIGS. 9A-B depict a quantified percentage of retained region of interest signal and retained interference obtained after projecting original data into a subspace corresponding with a subset of virtual coils, in accordance with various embodiments.

In various instances, Eq. (11) has been applied to measure the SIR of each virtual coil 830 (FIG. 8C), and also Eqs. (7) and (10) to separately quantify the signal energy 810 (FIG. 8A) and interference energy 820 (FIG. 8B) present in each virtual coil. Moreover, further data reflected in FIG. 9A illustrates a quantified percentage of retained ROI signal 910 and further data reflected in FIG. 9B reflects a quantified of retained interference 920 obtained after projecting the original data into the subspace corresponding to the top-$N_v$ ROVir coils. Specifically, assuming that the collection of $N_v$ weight vectors $w_j$ has been orthonormalized and that a matrix $W \in \mathbb{C}^{N_c \times N_v}$ is formed from the eigenvectors such that the jth column of W is equal to $w_j$, then $WW^H \in \mathbb{C}^{N_c \times N_c}$ is the unique orthogonal projection matrix for the span of the top-$N_v$ virtual coil combination weights [47]. As a result, the percentage of retained ROI signal can be computed as $$\frac{\|WW^H A W W^H\|_F}{\|A\|_F} \times 100\% \qquad (14)$$

and the percentage of retained interference can be computed as $$\frac{\|WW^H B W W^H\|_F}{\|B\|_F} \times 100\%. \qquad (15)$$

In thee above equations, $\|\cdot\|_F$ denotes the Frobenius norm in these expressions, which is a way to measure matrix energy.

Figure 7:
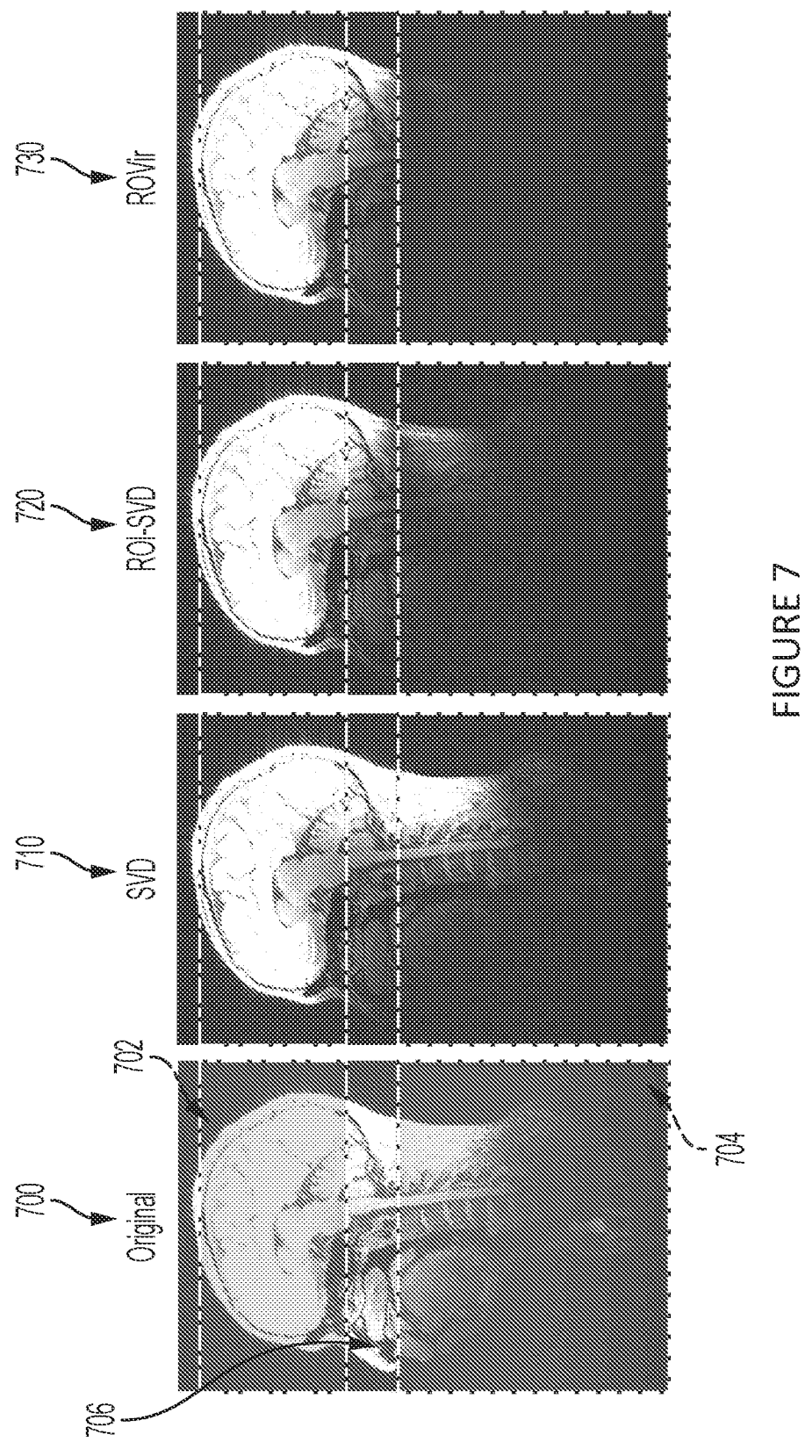
FIG. 7 depicts a quantitative comparison of various coil-compression techniques, in accordance with various embodiments.

Furthermore, since these mechanisms can also be viewed as a coil-compression technique in addition to an SIR-maximization technique, data reflected in FIG. 7 depicts a quantitative comparison between the disclosed approach and two popular SVD-based coil-compression techniques. The illustration labeled as "ROI-SVD" 720 is based on maximizing signal energy in the ROI using Eq. (12), using the same ROI $\Omega$ that is used the disclosed approach. The illustration labeled as "SVD" 710 is also based on maximizing signal using Eq. (12) but focuses on maximizing signal energy across the entire FOV without focusing narrowly on the ROI. This can be achieved by modifying the ROI $\Omega$ so that it equals the entire FOV. The illustration labeled "ORIGINAL" 700 is unprocessed, while the illustration labeled "ROVIR" 730 illustrates the quantitative comparison of the disclosed approach. Importantly, a ROI 702 and an area of unwanted signal 704 are marked for each illustration, showing the superior performance of the region-optimized virtual coil (ROVir) analysis discussed herein.

With reference to FIG. 7, there is provided a detailed/systematic quantitative evaluation of data generated by the ROVir analysis 730 with comparisons against data generated by SVD analysis 710 and data generated by ROI-SVD analysis 720 for a 2D sagittal brain imaging scenario, with real in vivo T1-weighted data acquired using a 32-channel array on a 3 Tesla scanner. These examples consider a situation where a region of interest 702 is the brain but not other parts of the head, neck, or torso (unwanted signal 704). As shown in illustration 700, the original coils have substantial sensitivity beyond just the brain.

Suppressing the unwanted signal from the head, neck, and torso could be beneficial in certain application scenarios. Not only could this enable the use of a smaller FOV without incurring aliasing artifacts, but it could also be useful for reducing gradient nonlinearity artifacts that could arise if one of the uninteresting parts of the image (e.g., the torso) is far away from isocenter. To accomplish this goal, a signal region $\Omega$ (region 702) is defined and an interference region $\Gamma$ (region 704) is defined. In some embodiments, regions 702, 704 are immediately adjacent, whereas in further instances, regions 702, 704 are designed as adjacent with an interstitial gap 706. This gap serves an analogous purpose to a "transition band" in digital filter design and radiofrequency pulse design and allows for better signal retention in the "passband" (e.g., $\Omega$) and better interference suppression in the "stopband" (e.g., $\Gamma$). In particular, since Maxwell's equations generally result in coil sensitivity maps that are spatially-smooth, it is difficult to sharply switch between retaining one region and suppressing an immediately-adjacent region, and overall performance can be substantially better if the transition is allowed to be more gradual.

FIG. 7 shows an image corresponding to data a set of thirty-two coils which has been processed by applying a root-sum-of-squares coil combination to the thirty-two channel datasets. The number of virtual channels $N_v$ of the set of coils was determined automatically to retain at least 95% of the signal from the region of interest.

The SVD approach 710 effectively compacts as much energy as possible from the full FOV into the first few virtual coils, causing the last few virtual coils to have very little information content. This allows for easy coil-compression by keeping the top $N_v$ virtual coils and discarding the remainder, although is not effective in suppressing interference—the first few SVD virtual coils still contain a substantial amount of energy from the neck and torso.

The ROI-SVD approach 720 may have slightly better characteristics than the SVD virtual coils within the ROI. Instead of compacting energy from the full FOV into the leading virtual coils, the ROI-SVD approach instead only compacts the energy from the ROI $\Omega$ into the first few virtual coils, without caring about what happens outside the ROI. As a result, the first few ROI-SVD virtual coils retain more ROI signal than the SVD virtual coils. However, there is still no attempt to suppress interference or separate signal from interference, and the first few ROI-SVD virtual channels can still contain a substantial amount of interference.

In contrast to both of these approaches, region-optimized virtual coil (ROVir) analysis 730 effectively compacts as much energy as possible from the ROI signal into the first few virtual coils while also compacting as much energy as possible from the interference region into the last few virtual coils. The middle virtual coils in between these two extremes contain relatively little energy from either the ROI signal or the interference.

As shown in FIG. 8-9B, the first few ROI-SVD virtual coils maximize the amount of signal from the ROI, although one may also observe that the difference between the amount of ROI signal between the first few ROI-SVD virtual coils and the first few ROVir coils is relatively small. Importantly, the first few ROVir coils have substantially better SIR values and substantially lower interference levels than the other two approaches.

In order to take advantage of the interference-suppression capabilities of ROVir, it is necessary to only keep the first few virtual coils, while discarding the rest. There are different strategies that could be used for this. One approach could be to set the number of virtual channels $N_v$ as the smallest number such that the percentage of retained signal is no smaller than a given tolerance. For example, if an implementation requires that at least 95% of the ROI signal is retained, curves shown in FIGS. 8A-9B permit a machine determination to use $N_v$=6 for ROVir analysis, $N_v$=5 for SVD analysis, and $N_v$=4 for ROI-SVD analysis. Using these $N_v$ parameters leads to the coil-combined root-sum-of-squares images 710, 720, 730 shown in FIG. 7. It is both visually and quantitatively discernable that ROVir retains substantially less interference (1.9%) than either SVD (98.0%) or ROI-SVD (4.0%), while by design, all three approaches have a similar amount of retained ROI signal (SVD: 98.1%; ROI-SVD: 98.3%; ROVir: 96.2%).

The previous approach to selecting $N_v$ prioritizes signal retention, but other approaches could also be applied if SIR or interference suppression were higher priorities. For example, a rule that prioritizes SIR might keep those virtual coils that have an SIR value that is larger than a given tolerance, e.g., keep only those virtual coils with SIR>2. This choice would lead to $N_v$=13 for ROVir (retained ROI signal=98.1%; retained interference=3.2%), $N_v$=10 for SVD (retained ROI signal=94.9%; retained interference=45.6%), and $N_v$=9 for ROI-SVD (retained ROI signal=99.98%; retained interference=8.8%). As another example, a rule that prioritizes interference suppression might choose $N_v$ as the largest number such that the percentage of retained interference is no larger than a given tolerance, e.g., choose $N_v$ under the constraint that the retained interference is <3%, which would lead to $N_v$=11 for ROVir (retained ROI signal=97.5%; retained interference=2.9%), $N_v$=1 for SVD (retained ROI signal=70.8%; retained interference=2.6%), and $N_v$=2 for ROI-SVD (retained ROI signal=82.2%; retained interference=2.4%). In all of these cases, ROVir demonstrates either substantially less interference for a similar amount of retained ROI signal or substantially more ROI signal for a similar amount of interference.

It should be noted that the plots shown in FIG. 8A-9B only describe a spatially-averaged summary of the retained ROI signal and interference characteristics, but do not provide information about their spatial distributions. To gain better insights into spatially-varying and $N_v$-dependent characteristics, data may be obtained corresponding to the relative image intensity (computed voxelwise, and shown as a percentage of the intensity that would be obtained using the full set of 32 coils) in the root-sum-of-squares images after projecting the data onto the subspace spanned by the top-$N_v$ virtual coils. These results show that the ROVir virtual coils can retain nearly 100% of the original ROI signal for most voxels within the ROI, while simultaneously very-substantially suppressing interference from all parts of the interference region. One notable limitation of ROVir relative to ROI-SVD is that ROVir appears to have attenuated the ROI signal near the transition band slightly more than ROI-SVD. However, this may be seen as a reasonable compromise given the superior capabilities for suppressing interference by ROVir systems and methods.

While the previous results explored the basic interference-suppression characteristics of ROVir with some amount of depth, the following sections are designed to illustrate more-quickly some of the potential uses of ROVir for a variety of different imaging applications.

One potential application of ROVir could be to reduce the size of the image support, enabling the use of a smaller FOV. Consider a non-cartesian imaging scenario where the same thirty-two channel sagittal brain dataset from the previous example is used to simulate spiral k-space data with a trajectory designed for a small FOV. Although the Nyquist criterion might be satisfied for an image with small spatial support, the data may be effectively undersampled for the actual image in this case.

If standard gridding-based reconstruction is applied to the original set of thirty-two coils and coil-combined using root-sum-of-squares, severe aliasing artifacts occur that contaminate most of the image. However, if prescan data were used to learn appropriate ROVir combination weights that suppress all signal except for that within a much smaller ROI, then these same combination weights can be directly applied to the undersampled spiral k-space data (or, equivalently, to the multichannel aliased images obtained after gridding reconstruction) to reduce the effective support of the image post facto, thereby avoiding the problematic aliasing artifacts. In each case, one may choose the $N_v$ parameter of ROVir automatically based on an SIR criterion, keeping all channels with SIR>1. This led to $N_v$=6 for an example imaging of a frontal lobe (with 95.3% retained signal but only 1.4% retained interference), $N_v$=7 for an example imaging of a occipital lobe (with 96.7% retained signal but only 2.8% retained interference), and $N_v$=2 for an example imaging of a vocal tract (with 56.0% retained signal but only 0.8% retained interference). In each of the different cases, the use of ROVir allows for a clear, aliasing-free depiction of the ROI. Importantly, all of these different results may be obtained from a same initial set of undersampled spiral k-space data and could have used the beam-steering capabilities of ROVir to target arbitrary other ROIs if so desired.

In effect, using ROVir in this way can be viewed as a virtual-coil based version of the parallel imaging with localized sensitivities (PILS) technique. In PILS, a specially-designed receiver array is utilized where the coil elements have localized and non-overlapping sensitivities. In contrast, instead of relying on specialized hardware design, we instead use the beam-steering capabilities of ROVir to construct virtual localized sensitivities from an original set of potentially-overlapping sensitivities. And unlike PILS, the ROVir coils do not have to be fixed prior to the experiment, they can instead be steered on-the-fly in real-time to meet the needs of the application, or even modified in post-processing long after the subject has left the scanner.

Similar to PILS, the ROVir approach can greatly simplify image reconstruction compared to traditional parallel imaging reconstruction methods, since image reconstruction can be performed using simple Fourier reconstruction techniques. This is quite different from more sophisticated reconstruction methods that must attempt to correct aliasing artifacts, potentially resulting in spatially-varying noise amplification. In addition, the fact that ROVir frequently uses $N_v$ values that are much smaller than $N_c$ can reduce data processing and memory requirements even further. Note also that, since the ROVir approach still often keeps more than one virtual coil, ROVir does not have to be used exclusively with simple Fourier reconstruction techniques, and can also be potentially used in combination with parallel imaging and/or other advanced reconstruction techniques to enable even further experimental accelerations.

One of the other important observations from this example is that the performance of ROVir varied considerably from the brain ROIs (where the retained signal was >95%) compared to the vocal tract ROI, where the retained signal was only slightly above 50% for a similar level of interference suppression. This difference in performance is highly related to the array geometry, since the soccerball-style headcoil that was used in this experiment was designed primarily for brain imaging and had fewer coil elements in close proximity to the mouth. This highlights the fact that the performance of ROVir may be highly dependent on both the characteristics of the signal ROI and interference region, as well as the geometry of the receiver array.

While the previous case showed sagittal non-cartesian brain imaging with a reduced FOV, the results for an example axial cartesian brain imaging show similar reduced FOV results for axial cartesian brain imaging, with data acquired at 3 Tesla using the same thirty-two channel head coil as in the previous case. In this case, retrospective uniform 3× undersampling of k-space lines along the anterior-posterior axis leads to classical cartesian aliasing artifacts for the original thirty-two channel data. ROVir was designed to retain signal from four different rectangular-shaped ROIs: anterior, central-anterior, central-posterior, and posterior. In each case, $N_v$ was selected automatically based on an SIR criterion, keeping all channels with SIR>2. This lead to the following parameters: $N_v$=4 for the anterior ROI (50.4% retained signal but only 0.1% retained interference); $N_v$=3 for the central-anterior ROI (19.7% retained signal but only 0.3% retained interference); $N_v$=4 for the central-posterior ROI (20.0% retained signal but only 0.4% retained interference); and $N_v$=6 for the posterior ROI (46.4% retained signal but only 0.5% retained interference). The use of ROVir is quite successful at reducing the effective size of the FOV, thereby mitigating aliasing artifacts. However, the quantitative numbers presented above also demonstrate that ROVir had better performance (e.g., better ROI signal retention) for the anterior and posterior ROIs than it did for the more centralized ROIs, which is again a reflection of the geometric characteristics of the receiver array, since the soccerball-style coil elements generally have more sensitivity to the periphery than to deeper parts of the brain.

ROVir concepts can also be potentially powerful for non-brain applications, such as reduced FOV cardiac imaging. By using ROVir to suppress regions that would otherwise cause aliasing, it is possible to achieve uniform undersampling (equivalent to assuming a smaller FOV) along the phase encoding dimension without incurring the major aliasing artifacts that would otherwise occur. Results for a four-chamber scan with retrospective 2× undersampling and results for a short-axis view with retrospective 3× undersampling indicate that, in both cases, $N_v$ was selected automatically based on an SIR criterion, keeping all channels with SIR>2. This resulted in $N_v$=4 for the four-chamber view (with 66.9% retained signal but only 0.2% retained interference) and $N_v$=5 for the short-axis view (with 90.6% retained signal but only 0.2% retained interference). Although both approaches are successful, it should be noted that substantially more signal was retained for the short-axis view compared to the four-chamber view, which is again related to the geometric characteristics of the receiver array in relation to the ROIs.

A brain imaging scenario provides another example use case that is typical of MR spectroscopic imaging (MRSI). For instance, consider an implementation to detect signal from brain parenchyma but to avoid potential contamination from strong signal originating from the scalp (e.g., extracranial lipid signals). Traditionally, extracranial signal is often avoided by combining spatially-selective excitation methods with outer-volume suppression methods. Unfortunately, this process can be imperfect, and unsuppressed extracranial signal remains a longstanding problem.

Again, ROVir techniques separate the brain parenchyma signal of interest from the extracranial interference. Various trade-offs are possible here between interference suppression and signal retention, and root-sum-of-squares images for two different extremes have been constructed, with $N_v$=2 (with 22.6% retained signal but only 0.2% retained interference) and $N_v$=28 (with 79.7% retained signal but only 36.1% retained interference).

This discussion described the ROVir framework, which applies theoretically-optimal beamforming principles to enable the suppression of uninteresting spatial regions and retention of interesting spatial regions. This is achieved by leveraging the spatial sensitivity variations inherent to multi-channel MRI data. The capability of ROVir was demonstrated in a number of different application scenarios, including brain, vocal tract, and cardiac imaging. Moreover, it should be noted that ROVir is completely compatible with existing hardware-, sequence-, and reconstruction-based approaches. Thus, further performance may be achieved through synergistic combinations of different approaches with that disclosed herein (ROVir). Moreover, while this discussion focused on the application of beamforming principles to linearly-mix the data from multiple coils, it is notable that similar implementations could also be applied to optimally linearly-mix other kinds of MRI data. For example, systems and methods may include applying beamforming principles to linearly-mix measured k-space data in order to perform optimal linear spatial localization (instead of relying on classical Fourier reconstruction techniques or other specialized linear estimation designs), or to apply beamforming principles to linearly-mix different contrast-encoded images to achieve optimal linear spectral-localization of different spectral tissue compartments in applications like multi-component diffusometry and relaxometry.

Thus, the preceding disclosure may be generalized for a variety of important applications. Combining reference to FIG. 1 and FIG. 3, the system for image reconstruction 2 by region-optimized virtual coil (ROVir) analysis may perform a method of image reconstruction 300 by region-optimized virtual coil (ROVir) analysis. The method 300 may include storing sensed data comprising at least one of image data or K-space data (block 310). For instance, an MRI machine may be a sensed data source 10 in operative communication with a processor 8. The processor 8 may receive the sensed data and store it in a sensed data storage memory 4.

The processor may determine coil combination weights that optimize a signal-to-interference ratio (SIR) of the sensed data (block 320). For instance, as discussed above, the processor 8 chooses the $\{w_{\ell j}\}$ coefficients needed to form optimal virtual coils by obtaining weight vectors $w_i$ and $w_j$ from a generalized eigenvalue decomposition.

The processor may also determine a region of interest and a region of non-interest of the sensed data (block 330). As mentioned, in some instances these regions are immediately adjacent, and in other instances these regions are separated by an interstitial area. This determination may be by user selection or may be by an implementation of artificial intelligence by the processor 8. The region of non-interest is filtered/removed from the sensed data (block 340).

Subsequently, the processor 8 generates or reconstructs a magnetic resonance imaging (MRI) image based on the sensed data and using the coil combination weights that were determined in block 320 (block 360). In this manner, a signal-to-interference ratio is optimized for the region of interest. Finally, the processor 8 transmits the generated or reconstructed MRI image to the user-readable display 6 which renders it (block 370).

Turning to FIG. 4, in various instances, a determination of coil combination weights that optimize an SIR of the sensed data has subsidiary aspects. One previously mentioned challenge is that of forming the A and B matrices. The potential challenge in forming these matrices is that prior knowledge of each of the individual sensitivity-weighted coil images $g_\ell(x)$ may be desirable.

As mentioned, this issue can be solved by forming images from prescan/calibration data and computing the optimal coil combination weights with respect to those images. The acquisition of prescan/calibration data is a part of some MRI protocols and the virtual coils obtained from such data has excellent SIR characteristics for any subsequent datasets as long as the relative spatial distribution of image energy is not substantially changed.

As such, FIG. 4 elaborates on a method of determining coil combination weights 320 that includes obtaining one or more scout scan images (block 410). A scout scan image corresponds to prescan/calibration data obtained by the MRI scanner. The method continues with determining a signal region within the one or more scout scan images (block 420). Such a determination may be by user input or by artificial intelligence computations. The method also includes determining an interference region within the one or more scout scan images (block 440). Such a determination may be by user input or by artificial intelligence computations. Consequently, coil combination weights based on the signal region and the interference region within the one or more scout scan images may be determined (block 450). Such coil combination weights may be selected to prioritize a signal region (ROI). The coil combination weights are determined to obtain the desired prior knowledge of each of the individual sensitivity-weighted coil images $g_\ell(x)$ so that the system may optimize the SIR of the sensed data.

Figure 5:
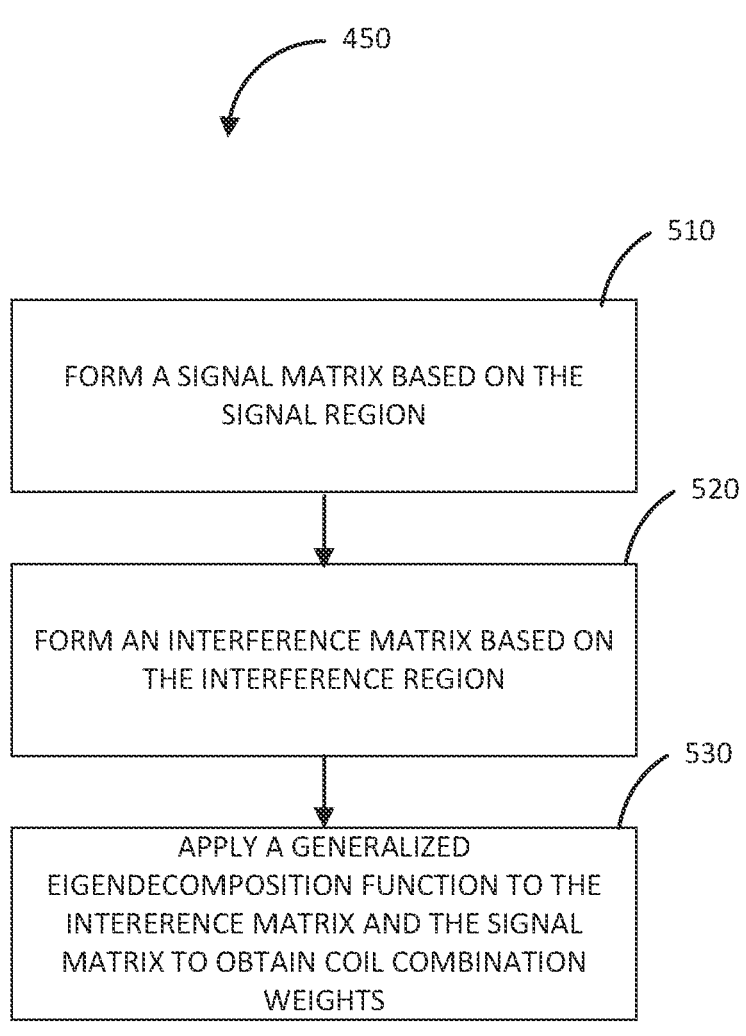
FIG. 5 depicts aspects of a method for determining coil combination weights based on a signal region and an interference region within one or more scout scan images, in accordance with various embodiments.

Determining coil combination weights based on the signal region and the interference region within the one or more scout scan images in block 450 may also include further aspects. Turning to FIG. 5, this determining process may include forming a signal matrix based on the signal region (ROI) (block 510). The signal region may be determined by user input or by artificial intelligence computations, as mentioned. The method may also include forming an interference matrix based on the interference region (block 520). Similar to the discussions herein above, mathematical functions may be applied to the combination of matrices to obtain coil combination weights that favors the region of interest. For instance, a generalized eigen decomposition function may be to the interference matrix and the signal matrix to obtain coil combination weights (block 530). These coil combination weights obtained from the prescan/calibration data obtained by the MRI scanner may then be stored in a computer memory to provide desirable prior knowledge of each of the individual sensitivity-weighted coil images $g_\ell(x)$. Stated differently, the virtual coils obtained from prescan/calibration data has excellent SIR characteristics for subsequent datasets.

What is claimed is:

1. An image reconstruction system, comprising:
a memory configured to store image data or k-space data; and
a processor coupled to the memory and configured to:
determine a region of interest of the image data or the k-space data,
determine a region of non-interest of the image data or the k-space data;
determine coil combination weights that optimize a signal-to-interference ratio of the image data or the k-space data based on the region of interest and the region of non-interest, and
generate or reconstruct a magnetic resonance imaging (MRI) image or k-space data based on the image data or the k-space data and using the coil combination weights.

2. The image reconstruction system of claim 1, further comprising:
a display configured to render the generated or reconstructed MRI image, wherein the processor is configured to output the generated or reconstructed MRI image on the display.

3. The image reconstruction system of claim 1, wherein the generated or reconstructed MRI image is generated faster than a second generated or reconstructed MRI image generated from an entire k-space data and with a same resolution.

4. The image reconstruction system of claim 1, wherein the generated or reconstructed MRI image is generated with greater resolution and during a same period of time than a second generated or reconstructed MRI image generated from an entire k-space data and with less resolution.

5. The image reconstruction system of claim 1, wherein the generated or reconstructed MRI image is generated with fewer artifacts than a second generated or reconstructed MRI image generated from an entire k-space data.

6. The image reconstruction system of claim 1, wherein the processor is further configured to:
filter, remove, or attenuate the region of non-interest of the image data or the k-space data from the image data or the k-space data; and
exclude or suppress the region of non-interest of the image data or the k-space data when generating or reconstructing the MRI image.

7. The image reconstruction system of claim 1, wherein the processor is further configured to:
obtain one or more scout scan images;
determine a signal region within the one or more scout scan images;
determine an interference region within the one or more scout scan images; and
determine the coil combination weights based on the signal region and the interference region within the one or more scout scan images.

8. The image reconstruction system of claim 7,
wherein the processor is further configured to:
obtain user input that indicates the signal region or the interference region within the one or more scout scan images; or
apply artificial intelligence to determine the signal region or the interference region within the one or more scout scan images, and wherein the processor is further configured to:

determine the signal region within the one or more scout scan images based on the user input or using the applied artificial intelligence.

9. The image reconstruction system of claim 7, wherein the coil combination weights prioritize the signal region over the interference region.

10. The image reconstruction system of claim 7, wherein to determine the coil combination weights the processor is further configured to:

form a signal matrix based on the signal region;

form an interference matrix based on the interference region; and determine the coil combination weights based on the signal matrix and the interference matrix using a generalized eigen decomposition function.

11. An image reconstruction system, comprising:

a memory configured to store image data or k-space data; and a processor coupled to the memory and configured to:

determine a region of interest of the image data or the k-space data;

determine a region of non-interest of the image data or the k-space data;

determine coil combination weights that optimize a signal-to-interference ratio (SIR) of the image data or the k-space data based on the region of interest and the region of non-interest;

generate or reconstruct a magnetic resonance imaging (MRI) image based on the region of interest of the image data or the k-space data; and transmit the generated or reconstructed MRI image for display.

12. The image reconstruction system of claim 11, further comprising a display configured to render the generated or reconstructed MRI image.

13. The image reconstruction system of claim 11, wherein the processor is further configured to:

filter, remove, or attenuate the region of non-interest of the image data or the k-space data from the image data or the k-space data; and exclude or suppress the region of non-interest of the image data or the k-space data when generating or reconstructing the MRI image.

14. The image reconstruction system of claim 11, wherein the processor is further configured to:

obtain one or more scout scan images;

determine a signal region within the one or more scout scan images;

determine an interference region within the one or more scout scan images; and determine the coil combination weights based on the signal region and the interference region within the one or more scout scan images.

15. The image reconstruction system of claim 14, wherein the processor is further configured to:

obtain user input that indicates the signal region or the interference region within the one or more scout scan images, wherein the processor is further configured to determine the signal region within the one or more scout scan images based on the user input.

16. The image reconstruction system of claim 11, further comprising:

a magnetic resonance imaging (MRI) scanner configured to obtain the image data or the k-space data, wherein the image data or the k-space data is representative of data related to a human body.

17. The image reconstruction system of claim 16, wherein the data related to the human body includes biological, anatomical, neurological, functional, microstructural, or physiological data of the human body.

18. A method of generating a magnetic resonance imaging (MRI) image, comprising:

obtaining, by a processor, image data or k-space data;

determining, by the processor, a region of interest of the image data or the k-space data;

determining, by the processor, a region of non-interest of the image data or the k-space data;

determining, by the processor, coil combination weights that optimize a signal-to-interference ratio of the image data or the k-space data based on the region of interest and the region of non-interest; and generating or reconstructing, by the processor, the MRI image based on the image data or the k-space data using the coil combination weights.

* * * * *